US011730936B2

(12) United States Patent
Hendriks et al.

(10) Patent No.: US 11,730,936 B2
(45) Date of Patent: Aug. 22, 2023

(54) APPLICATOR DEVICE

(71) Applicant: MEDICAL BRANDS RESEARCH B.V., Amsterdam (NL)

(72) Inventors: Maikel Hendriks, Amsterdam (NL); Pieternella Anna Maria Bouter, Amsterdam (NL)

(73) Assignee: MEDICAL BRANDS RESEARCH B.V., Amsterdam (NL)

(*) Notice: Subject to any disclaimer, the term of this patent is extended or adjusted under 35 U.S.C. 154(b) by 1079 days.

(21) Appl. No.: 16/346,595

(22) PCT Filed: Nov. 8, 2017

(86) PCT No.: PCT/EP2017/078588
§ 371 (c)(1),
(2) Date: May 1, 2019

(87) PCT Pub. No.: WO2018/087140
PCT Pub. Date: May 17, 2018

(65) Prior Publication Data
US 2019/0255305 A1    Aug. 22, 2019

(30) Foreign Application Priority Data

Nov. 8, 2016  (EP) .................................... 16197752
Dec. 13, 2016 (EP) .................................... 16203647

(51) Int. Cl.
*A61M 35/00*   (2006.01)
*A61K 8/36*    (2006.01)
(Continued)

(52) U.S. Cl.
CPC ......... *A61M 35/003* (2013.01); *A45D 34/042* (2013.01); *A61K 8/36* (2013.01);
(Continued)

(58) Field of Classification Search
CPC ............... A61M 35/003; A45D 34/042; A45D 2200/055; A61K 8/36; A61K 8/8147; B65D 83/0005
See application file for complete search history.

(56) References Cited

U.S. PATENT DOCUMENTS 3,768,509 A * 10/1973 Goda .................... F16K 15/046
                                                 137/539
4,189,801 A    2/1980 Lanusse
(Continued)

FOREIGN PATENT DOCUMENTS

CN      101069671      11/2007
EP      1 277 595       1/2003
(Continued)

OTHER PUBLICATIONS

Official Action, CN Application No. 201780068687.4 dated Feb. 2, 2021.
(Continued)

*Primary Examiner* — Susan S Su
*Assistant Examiner* — Eric Rassavong
(74) *Attorney, Agent, or Firm* — Nixon & Vanderhye P.C.

(57) ABSTRACT

The invention relates to an applicator device comprising an applicator tip and a container part, wherein the container part comprises: (i) a container comprising a container wall, a valve, and a plunger, wherein the container wall, the valve, and the plunger together define a storage volume for containing a liquid, wherein the plunger comprises a circumferential wall, sealingly contacting the container wall; and (ii) a plunger advance system functionally coupled to the plunger and configured to advance the plunger for reducing the storage volume for expelling at least part of the liquid via said valve to said tip, wherein the plunger advance system is arranged outside the storage volume; wherein (a) the valve comprises a first spring system comprising a first spring (Continued)

material comprising a stainless steel material comprising a molybdenum content selected in the range of 0.5-7 wt. %, and (b) the plunger advance system comprises a second spring system comprising a second spring material comprising a stainless steel material comprising a molybdenum content selected in the range of 0.5-7 wt. %, applies; and the plunger advance system comprises a polymer selected from the group consisting of polypropylene (PP), ethylene chlorotrifluoroethylene (ECTFE), and polyoxymethylene (POM); and wherein the plunger advance system comprises a spindle system comprising a ratchet system comprising a first element and a second element, wherein the second spring system is configured to provide the first element and the second element to engage on each other.

20 Claims, 3 Drawing Sheets

(51) Int. Cl.
  *A61K 8/81* (2006.01)
  *A45D 34/04* (2006.01)
  *B65D 83/00* (2006.01)
(52) U.S. Cl.
  CPC ........ *A61K 8/8147* (2013.01); *B65D 83/0005* (2013.01); *A45D 2200/055* (2013.01)

(56) References Cited

U.S. PATENT DOCUMENTS

| | | | | |
|---|---|---|---|---|
| 4,693,684 | A * | 9/1987 | Blatherwick | A61C 5/62 433/90 |
| 5,827,002 | A * | 10/1998 | Nakajima | A45D 34/042 401/172 |
| 6,918,511 | B1 * | 7/2005 | Spatz | B65D 83/0011 401/175 |
| 7,153,053 | B1 * | 12/2006 | Wiley | A45D 40/24 401/219 |
| 2005/0025558 | A1 | 2/2005 | Severa | |
| 2005/0077315 | A1 * | 4/2005 | Pavlu | B05B 11/3092 222/1 |
| 2008/0107475 | A1 * | 5/2008 | Wojcik | A61M 35/003 401/219 |
| 2009/0052971 | A1 * | 2/2009 | Pires | G01F 11/025 222/137 |
| 2010/0308082 | A1 * | 12/2010 | Lambie | B05B 11/0038 222/162 |
| 2011/0293354 | A1 | 12/2011 | Dwyer | |
| 2012/0328354 | A1 * | 12/2012 | Koyama | A45D 34/042 401/179 |
| 2013/0336703 | A1 * | 12/2013 | Katz | A45D 40/20 401/102 |
| 2016/0151803 | A1 * | 6/2016 | Arwatz | B05C 17/0103 401/172 |
| 2016/0220327 | A1 * | 8/2016 | Tapocik | A61M 5/31581 |
| 2017/0016470 | A1 * | 1/2017 | Herre | F16B 35/007 |

FOREIGN PATENT DOCUMENTS

| | | | | |
|---|---|---|---|---|
| EP | | 2 223 811 | 9/2010 | |
| WO | WO-2012007584 | A2 * | 1/2012 | ............. A61K 31/19 |
| WO | WO-2014045277 | A1 * | 3/2014 | ............. A61K 31/19 |

OTHER PUBLICATIONS

Extended European Search Report for EP 16 20 3647 dated Jun. 15, 2017, 4 pages.
International Search Report for PCT/EP2017/078588 dated Feb. 8, 2018, 6 pages.
Written Opinion of the ISA for PCT/EP2017/078588 dated Feb. 8, 2018, 11 pages.

* cited by examiner

APPLICATOR DEVICE

This application is the U.S. national phase of International Application No. PCT/EP2017/078588 filed Nov. 8, 2017 which designated the U.S. and claims priority to EP Patent Application Nos. 16197752.5 filed Nov. 8, 2016 and 16203647.9 filed Dec. 13, 2016, the entire contents of each of which are hereby incorporated by reference.

FIELD OF THE INVENTION

The invention relates to an applicator device and its use.

BACKGROUND OF THE INVENTION

Various compositions are known for the treatment of skin lesions, such as warts, corns and calluses, actinic keratosis, keratosis pilaris, acne, tattoo removal/correction, skin hyperpigmentation and/or nail lesions, such as ingrown toenails and/or lesions in mucous membranes, such as cold sores and mouth ulcers. WO2012007584, for instance, describes a composition for the treatment of superficial lesions, in particular skin lesions, mucous membrane lesions and/or nail lesions, an applicator comprising such a composition and the use of such a composition. The composition comprises an effective amount of trichloroacetic acid, at least one thickener, and at a physiologically acceptable solvent. The composition is considered effective against a plethora of superficial lesions selected from the group consisting of viral warts, verrucae, water warts (molluscum contagiosum), corns and calluses, and skin hyperpigmentation: age spots, solar lentigo, senial lentigo, acne, keratosis pilaris, actinic keratosis, mouth ulcers (canker sores), cold sores, ingrown toenails, onychomycosis, eyelid xanthelasma.

WO2007139378 describes a device for cold treating a tissue. The invention also relates to an assembly of such a device and a container comprising a cryogenic liquid, such as a spray can. The invention further relates to a method for cold treating a tissue.

WO2012007584 describes a composition for the treatment of superficial lesions, in particular skin lesions, mucous membrane lesions and/or nail lesions, an applicator comprising such a composition and the use of such a composition. The composition comprises an effective amount of trichloroacetic acid, at least one thickener, and at a physiologically acceptable solvent and is effective against a plethora of superficial lesions selected from the group consisting of viral warts, verrucae, water warts (molluscum contagiosum), corns and calluses, and skin hyperpigmentation: age spots, solar lentigo, senial lentigo, acne, keratosis pilaris, actinic keratosis, mouth ulcers (canker sores), cold sores, ingrown toenails, onychomycosis, eyelid xanthelasma.

US2005025558 describes a dispensing device for substances including personal care, cosmetics, and medicinal substances. The device dispenses a metered amount of a substance by actuation of a push button which indirectly contacts an advancable shaft, thereby driving a piston to push the substance from a reservoir into an applicator. The device can be operated in one hand of a person and is devoid of any twist or rotation mechanism.

US20100308082 describes a device for dispensing a substance having a dispensing outlet from which the substance is dispensable, a dispensing member mounted for movement in a dispensing direction from a first position to a second position, said movement, in use, causing the substance to be dispensed from the dispensing outlet, and an actuator mechanism for moving the dispensing member from the first position to the second position. The actuator mechanism has a first member mounted for movement in a predetermined direction and a second member pivotally mounted on the first member for pivotal movement in a predetermined pivotal sense. The actuator mechanism is adapted such that movement of the first member in the predetermined direction results in the second member moving therewith and pivoting in the predetermined pivotal sense and said pivotal movement of the second member in the predetermined pivotal sense results in the dispensing member moving from the first position to the second position.

EP2223811 decribes an applicator that can eject an application liquid in an approximately constant amount without regard to the viscosity of the application liquid. The applicator is constructed such that when the user clicks rear end of an inner barrel, the aftermentioned valve mechanism is actuated by moving the inner barrel relative to outer barrel, whereby an application liquid is supplied to applying element arranged at front end part of outer barrel, and that when valve seat member and valve rod member move relatively to each other, the valve mechanism can take the first state in which piston portion on the front side of valve rod member comes into sliding contact with front-side liquid-tight portion inside the valve seat member, the second state in which both of piston portion on the front side of valve rod member and piston portion on the rear side of valve rod member do not come in sliding contact with the corresponding liquid-tight portions inside the valve seat member, and the third state in which piston portion on the rear side of valve rod member comes into sliding contact with rear-side liquid-tight portion inside valve seat member.

EP1277595 decribes an applicator comprising a tubular main shaft body containing therein a liquid, a compressive device, disposed at a rear portion of the tubular main shaft body, for compressing the liquid, a non-return device positioned at a rear portion of the liquid and movable along with a decrease of the liquid, and a valve mechanism between the non-return device and the compressive means.

US2011293354 describes an airless applicator that may deliver high/low viscosity liquids or semi-liquids, and contains a valve controlling flow between a product reservoir and an intermediate pooling area, while a narrow opening between the intermediate pooling area and a product dispensing chamber controls flow therebetween. This arrangement prevents backflow to the product reservoir, precluding an influx of contamination therein. Product delivery is by specially adapted applicator heads.

SUMMARY OF THE INVENTION

Many prior art methods to treat warts or other skin lesions are not effective or not effective enough. Further, some of the prior art methods need specific care and medical supervision, such as the treatment of warts with liquid nitrogen. Further, many of the prior art applicators comprise materials that deteriorate in time. Especially, some prior art applicators may not be durable. Furthermore, many of the prior art applicators do not provide a dosage control of a treatment liquid.

Hence, it is an aspect of the invention to provide an alternative method and/or applicator, which preferably further at least partly obviate one or more of the above-described drawbacks, and which is especially safe.

In a first aspect, the invention provides an applicator device. The applicator device ("applicator" or "device")

comprises an applicator tip and a container part. The container part comprises: (i) a container comprising a container wall, a valve, and a plunger, wherein the container wall, the valve, and the plunger together define a (variable) storage volume, especially for containing a liquid, such as an acidic liquid, wherein the plunger comprises a circumferential wall, sealingly contacting the container wall; and (ii) a plunger advance system functionally coupled to the plunger and configured to advance the plunger for reducing the storage volume for expelling at least part of the liquid via said valve to said tip, wherein the plunger advance system is arranged outside the storage volume. Especially, one or more of (a) the valve comprises a first spring system comprising a first spring material especially selected from the group consisting of a noble metal, polypropylene, and a stainless steel material, especially a stainless steel material, especially the stainless steel material comprising a molybdenum content selected in the range of 0.1-7 wt./%, such as in the range of 0.5-7 wt. %, especially in the range of 2-7 wt. %, and (b) the plunger advance system comprises a second spring system comprising a second spring material especially selected from the group consisting of a noble metal, polypropylene, and a stainless steel material, especially comprising a molybdenum content selected in the range of 0.1-7 wt. %, such as in the range of 0.5-7 wt. %, especially in the range of 2-7 wt. %, applies. In specific embodiments, the valve comprises the first spring system and the plunger advance system comprises the second spring system. Further, in specific embodiments the plunger advance system comprises a polymer selected from the group consisting of PP (polypropylene), ECTFE (ethylene chlorotrifluoroethylene) and POM (polyoxymethylene), especially polypropylene or ethylene chlorotrifluoroethylene, even more especially polypropylene.

In embodiments, in an open position of the valve, the applicator tip is in fluid connection with the storage volume and in a closed position of the valve, the applicator tip is in closed fluid connection with the storage volume. In the open position of the valve, a fluid, especially the liquid, may flow through the valve. In the closed position of the valve, no fluid, especially no liquid, may flow through the valve. Hence, in a closed position the fluid connection is (temporarily) intercepted.

The applicator device described herein is especially configured for holding a liquid. Herein the term "liquid" relates to a flowable fluid, especially having a viscosity at room temperature ranging from about 0.1 mPa·s (cP) to 1000 Pa·s, especially selected in the range of 0.2 mPa·s-250 Pa·s, even more especially in the range of 1 mPa·s-60 Pa·s, such as in the range of 1 Pa·s-15 Pa·s, especially in the range of 2.5 Pa·s-10 Pa·s (2500 cP-10000 cP) Hence, the term "liquid" may also relate to a "gel", a "paste", or a "semi-solid". In embodiments, the viscosity of the liquid (gel) is selected around 6000 mPa·s, such as in the range of 4000-8000 mPa·s at 25° C. (see also below, including the method to determine the viscosity). The liquid especially has a flowability allowing it to be expelled from the storage volume by manual application, with e.g. a thumb, of the plunger advance system.

The liquid may comprise a composition. The composition is preferably a fluid, in order to enable easy application and dividing the active ingredient on a skin or nail surface. Fluids include liquid and gel compositions, as well as semi-solid compositions. Herein the terms "liquid" and "treatment liquid" especially relate to "a composition" and vice versa. The liquid/composition may comprise trichloroacetic acid (TCA), see further below. In further embodiments, the composition does not comprise trichloroacteic acid. In yet further embodiments, the composition does not comprise any acid (see also below). The composition can be used in for instance a skin peeling treatment, for the medical or cosmetic treatment of skin lesion selected from the group consisting of warts, corn and calluses, and for nail treatments including ingrown toenails. A postulated mechanism of action is that the composition comprising TCA softens the skin or nail, and enables to peel the skin or nail lesion away. For severe lesions, multiple treatments may be needed. Both cosmetic and medical treatments may be performed with the compositions according to the invention. Other active ingredients contributing to the treatment of the lesion may be added. For instance salicylic acid is another component effective in corroding the skin or nails, and may be used as an additional active ingredient in combination with trichloroacetic acid.

The liquid carrier may be a single solvent or mixture of solvents and additives capable of dissolving of mixing with the concentration of TCA used. A preferred liquid carrier is water or a water-based mixture. Water may be mixed with an organic solvent. It is also possible to use a water-free carrier, preferably using easily evaporable solvents. The use of evaporable solvents makes it possible to achieve a relatively high concentration of TCA at a treated location on the skin or nail. Suitable evaporable solvents include methanol, ethanol, propanol, methyl ethyl ketone, acetone, ethyl acetate, and mixtures thereof.

The thickener provides the composition with an increased viscosity, making it easier to focus the active ingredient on the intended location on the skin or nails, preventing to some extend the spreading of the composition to locations where its action is not desired. Also, the thickener improves the time the active ingredient remains on a treated surface, improving the efficacy of the composition. The thickener may be a single compound, but may also comprise a mixture of compounds. The thickener is preferably a gel-forming agent compatible with the liquid carrier used.

Preferably, the composition has a viscosity of at least 3000 mPas as measured using rotary viscometry at 25° C. Viscosity is measured according to the rotating viscosimeter protocol in the European Pharmacopeia Ph. Eur (01/2005:20210) Ph. Eur. 5th edition vol 1, p. 29, chapter 2.2.10. Such compositions have a significant adhering effect on skin and/or nail, allowing for spot treatment. Compositions with viscosities up to about 60.000 mPas are considered to be useful; liquid compositions with higher viscosities are considered to be difficult to handle.

In a preferred embodiment, the composition is a sprayable liquid having a viscosity in the range of about 1.0 mPas to about 2000 mPas at 25° C. Spraying is an easy and fast way to apply the composition to a surface to be treated.

In another preferred embodiment, the composition has a viscosity of at least 5000 mPas as measured at 25° C. according to the rotating viscosimeter protocol in the European Pharmacopeia Ph. Eur (01/2005:20210) Ph. Eur. 5th edition vol 1, p. 29, chapter 2.2.10. Rotating Viscometer Method. Such a viscosity gives the composition a particularly useful adhering effect on skin and nails. Preferably, the composition is a gel composition having a viscosity in the range of about 3000 mPas to 60000 mPas at 25° C. The gel composition is relatively easy to apply, either manually or by using a suitable applicator, and combines a relatively large adhering effect. The gel is particularly suitable to apply the composition selectively to a specific spot, such as a wart.

Preferably, the composition has a viscosity in the range of 450 mPas to 10000 mPas at 25° C., more preferably from 5000 mPas to 10000 mPas at 25° C. Such a composition shows a sufficient adhering effect, while still being relatively easy to apply and process. It is advantageous if the liquid carrier is an aqueous carrier. A water-based composition is relatively easy to prepare, and dissolves TCA well. The water may be mixed with other solvents, for instance C1-C6 alcohols or ketones, and additives such as surfactants. Preferably, the liquid carrier consists for at least 50% of water.

Preferably, the composition has a pH below 4. Low pH compositions appear to provide a better treatment results. In addition, the low pH compositions appear to have an additional effect in suppressing microbiological threats on the skin and nail, including bacteria, fungus and yeast, in particular onchyomycosis (nail fungus).

In a preferred embodiment, the composition comprises at least 1% trichloroacetic acid, more preferably at least 20% w/w trichloroacetic acid, more preferably in the range of 20-50% w/w. Compositions having a concentration of at least 20% w/w show good results in treating skin and nail lesions within a relatively short treatment. Although skin irritations occasionally occur after treatment with TCA concentrations below 50%, TCA concentrations over 50% were found to significantly increase the chance of skin irritations.

It is preferred if the thickener comprises at least a thickener selected from a polysaccharide thickener, a cross-linked acrylic acid polymer and polysiloxanes, or mixtures thereof. These thickeners show a good compatibility with trichloroacetic acid. Polysaccharide thickeners showed in addition to their thickening effect to decrease the chance of skin irritations.

In a preferred embodiment, the thickener comprises at least one thickener selected from the group consisting of amylose, amylopectine, carbopol, silicones, Xanthan gum, agar-agar, polydimethylsiloxane (and mixes thereof), dimethicones, carrageen, cellulose, carboxymethyl cellulose or salts thereof, ethyl cellulose, hydroxypropyl cellulose and methyl cellulose, natural rubber, beeswax, lanolin, petrolatum, paraffin, rosin (and mixtures thereof). The viscosity of the formulation having excellent adhering effects may be achieved using these thickeners. Carbopol is a brand name for cross-linked polymers of acrylic acid, and includes the commercially available products Carbopol 71G NF, Carbopol 971P NF, Carbopol 974P NF, Carbopol 934P NF, Carbopol 980P NF, Carbopol 981P NF, Carbopol 5984EP, Carbopol ETD 2020 NF, Carbopol 934 NF, Carbopol 934P NF, Carbopol 940 NF, Carbopol 941 NF, Carbopol 1342 NF, Pemulen TR-1 NF, Pemulen TR2-NF, Noveon AA-USP, and Carbopol Ultrez 10 NF.

Preferably, the thickener remains essentially stable in the presence of trichloroacetic acid. Some thickeners are degraded in the presence of TCA, resulting in a coloured product, which may appear less attractive to some persons. Also, the color of a solution may be difficult to control in case a colorant was used. A colourless composition is generally considered to be visually more attractive and therefore more desirable.

Most preferably, the thickener comprises carbopol. Carbopol shows an excellent stability in the presence of TCA, allowing for colorless compositions, or excellent color control in case the composition comprises a colorant. Carbopol polymers, also called carbomers, are polymers of acrylic acid cross-linked with polyalkenyl ethers or divinyl glycol.

Carbopol allows for an excellent control of the viscosity of the formulation (of the treatment liquid). Preferably, the composition comprises at least 0.5% w/w carbopol, preferably in the range of 0.5-3% w/w. Compositions comprising 0.5%-1% w/w carbopol are excellent for sprayable products, products comprising 1.5-2.5% w/w form a well-applicable gel. Products comprising carbopol more than 3% w/w may become too rigid for easy processing and application. Hence, in embodiments, the liquid comprises a gel, especially wherein the liquid comprises trichloro acetic acid and cross-linked polymers of acrylic acid, especially carbopol. These cross-linked polymers are especially polymers of acrylic acid cross-linked with polyalkenyl ethers or divinyl glycol.

In a preferred embodiment, the composition comprises a combination of carbopol and glycerin. Although glycerin is by itself not a thickener, the addition of glycerin to a composition according to the invention using carbopol yields an increase in viscosity. Thus, the cost price for a formulation with a relatively high viscosity may be reduced by using less of the relatively expensive carbopol by adding the relatively cheap glycerin. Preferably, glycerin is added in an amount ranging from approximately 1% w/w to approximately 20% w/w. As an additional effect, glycerin was found to reduce the chance of skin irritation by TCA.

In embodiments, the liquid (composition) may have a pH less than 7. In embodiments, the liquid comprises an acid. In further embodiments, the liquid comprises trichloro acetic acid. Yet, in other embodiments, the liquid (the composition) may comprise a caustic liquid, especially having a pH more than 7. The liquid may further comprise a corrosive liquid. The liquid may also comprise a liquid comprising a substantially neutral pH, especially a pH in the range of 6-8. The applicator may especially be configured for containing an acid, especially for containing trichloro acetic acid (in the (variable) storage volume). Especially, the pH of the liquid is equal to or lower than 4.

The container part may have an elongated shape. The container part may comprise a syringe-like shape. In embodiments, the container part comprises a pen-like shape. The container part may also have another type of shape and/or other relative dimensions. The container part may, e.g., comprise a disk-like shape or any other shape. Especially, the container part comprises an elongated shape having a longitudinal axis or (container part) body axis.

The storage volume is especially variable and may reduce when the applicator is in use, especially when the plunger is advanced (for expelling at least part of the liquid). Herein "advancing the plunger for reducing the storage volume" especially relates to a translation of the plunger along a longitudinal axis of the storage volume, especially in the direction towards the valve. Hence, at least a first part of the container wall is configured adjacent to the storage volume, i.e., especially contacting (a liquid in) the storage volume. A second part of the container wall may not be arranged adjacent to the storage volume, especially when the plunger is advanced. Especially, said second part of the container wall may be adjacent to the plunger advance system, and especially may not contact a liquid. During advancing the plunger a ratio of (an area of) the first part of the container wall to (an area of) the second part of the container wall may decrease, especially also reducing the variable storage volume.

The longitudinal axis of the container part may comprise the longitudinal axis of the storage volume. Essentially, they may coincide.

The plunger especially sealingly contacts the container wall with at least part of the circumferential wall (of the plunger). When the plunger is advanced, the liquid may be transported in a direction towards the valve. Successively, a part of the liquid may be expelled from the applicator via the tip.

Herein the term "sealingly" in "sealingly contacting" and the like may especially relate to preventing a liquid to (essentially) pass (such sealing contact). The liquid may (substantially) not pass the circumferential wall (of the plunger) (when the plunger is advanced). However, the plunger may nevertheless be movable relative to the container wall, especially in a direction essentially parallel to the threaded shaft (see below). Hence, the plunger is especially movable relative to the container wall in a direction essentially parallel to a body axis of the device. Especially, the plunger is movable relative to the container wall in a direction essentially parallel to the longitudinal axis of the storage volume and/or the circumferential wall.

Essentially, a surface of the plunger is defined by the circumferential wall, a first end and a second end (arranged opposite to the first end). The circumferential wall may especially bridge the first end and the second end. Especially, a longitudinal axis of the plunger comprises the first end and the second end. The term "circumferential wall" especially relates to a wall (of the plunger) comprising the perimeter of the plunger. In embodiments, the circumferential wall comprises a circular shape. Said perimeter does not necessarily need to be a circular perimeter. In further embodiments, said wall may comprise a non-circular shape, such as a rectangular shape or an oval shape.

The container may have a circular (container) cross sectional area (or cross section) perpendicular to the longitudinal axis of the storage volume (especially an inner cross sectional area not comprising the container wall). The container cross sectional area (also) does not necessarily need to be circular. The container cross sectional area ("container cross section") may have any arbitrary shape. In embodiments, the container cross section has a rectangular shape, such as a square shape. In further embodiments, the container cross section has an oval shape. Essentially, the shape of the circumferential wall (of the plunger) relates to (especially matches) the shape of the container cross section to provide a sealing contact between the plunger and the container wall. Especially, the cross section of the container is circular and especially the circumferential wall (of the plunger) comprises a circular shape.

Especially, a shape of the plunger and the shape of the circumferential wall are alike. The plunger may further comprise a cylindrical shape, especially comprising the circular shape. Alternatively or additionally, the plunger may comprise a conical shape (comprising the circular shape).

Experimentally it was found that embodiments comprising a cylindrical shaped plunger, wherein a cross sectional area of the plunger is substantially constant along the longitudinal axis of the plunger, may still allow small amounts of the liquid to leak along the circumferential wall of the plunger. It was further found, that by selecting a plunger comprising a conical shape, especially a double cone shape, such leaking was prevented.

The term "double cone shape" especially relates to a shape comprising a first tapered part, optionally comprising the first end of the plunger, and a second tapered part, optionally comprising the second end of the plunger. Especially, a cross section of the first tapered part closer to the second tapered part is smaller than a cross section (of the first tapered part) closer to the first end. Especially, (also) a cross section of the second tapered part closer to the first tapered part is smaller than a cross section (of the second tapered part) closer to the second end. Herein, the term cross section of a (first or second) tapered part especially relates to a cross section perpendicular to the longitudinal axis of the plunger. The cross section of the plunger may be smallest at a location between the first end and the second end. Especially, the first tapered part and/or the second tapered part includes a cylindrical part. Such plunger may (also) comprise a concavely shaped (such as a pinched waist shaped) circumferential wall. Such concave shape may be provided by the first and the second tapered parts.

In further advantageous embodiments (also) at least one of the first and the second end of the plunger may comprise a concave shape. In embodiments, the plunger is reinforced adjacent to at least one of the first end and the second end of the plunger. The plunger may, e.g., be reinforced by configuring the circumferential wall thicker near the end of the plunger (compared to at locations at the circumferential wall between the ends. Especially, the circumferential wall comprises a concave circumferential wall. Herein, the term "concave" may relate to a gradually changing shape. Said term may also relate to a more discretely changing shape, especially overall providing the concave shape. In embodiments, the plunger comprises one or more (polymer) materials selected from the group consisting of PP (polypropylene) and EVA (ethylene vinyl acetate), especially ethylene vinyl acetate. Ethylene vinyl acetate may be flexible and provide a sealing contact with the container wall. EVA may further be resistant against specific liquids, such a liquid comprising TCA. In embodiments, the plunger, especially the circumferential wall, may further comprise a coating and/or a seal, such as a ring seal. In embodiments, the plungers comprises, especially (substantially) consists of, ethylene vinyl acetate.

Especially, the plunger comprises a double cone shape and further especially comprises EVA.

The plunger advance system comprises a polymer (polymeric) material. Especially, the plunger advance system further comprises the second spring material. In embodiments, the polymer material comprises polypropylene and ethylene vinyl acetate. Especially, the polymer material substantially only comprises polypropylene and ethylene vinyl acetate, especially wherein the remainder of the polymer material is comprises, especially consists of polypropylene. In further embodiments, the second spring material, and especially also the first spring material, comprises, especially consists of, stainless steel 316.

The plunger advance system is especially arranged outside the storage volume. The liquid, especially an aggressive liquid (i.e. incompatible with materials it contacts) may thus especially not contact the plunger advance system. Yet, it was surprisingly found that the plunger advance system (especially elements (see below) of the plunger advance system) may (still) deteriorate over a relatively short period (such as a couple of months) when aggressive liquids (such as liquids comprising TCA at higher concentrations, as described herein) are used. Even when there is no leakage of the aggressive liquid it was noticed that at least part of the plunger advance system may deteriorate with time. Surprisingly, this problem appeared to be only solved when specific combinations of materials were used.

The applicator according to the invention, yet, is configured to allowing comprising the liquid described above, especially TCA, wherein the applicator may (hardly) not degenerate in time (see further below). Especially, the applicator may be durable, and may function properly over a period of at least one year, such as at least 2 years.

Essentially, the plunger advance system is configured to actuate the plunger, especially to advance the plunger, especially for reducing the storage volume, especially to expel the (treatment) liquid. In embodiments, the plunger advance system comprises a plunger rod (functionally coupled to the plunger) to actuate the plunger. The applicator device may be used over a longer period and especially the liquid is not expelled in one go. Hence, the plunger advance system is especially configured for expelling a determined amount of treatment liquid. The plunger advance system is especially configured for (recurrently) expelling a controlled dosage of the (treatment) liquid.

In further embodiments, the plunger advance system comprises a spindle system. Especially, the spindle system comprises a thread driven spindle system. Such spindle system may comprise a threaded shaft and a screw cap. The screw cap (comprising a (internal) screw-thread) may be configured around the threaded shaft. Especially the screw-thread ("thread") of the threaded shaft and the screw-thread of the crew cap fit together/engage on each other (see further below). The threaded shaft may rotate (in the screw cap) relative to the screw cap. Especially such rotation may provide a translation of the threaded shaft relative to the screw cap. The treaded shaft may comprise a round (cylindrical) shape. In further embodiments, the threaded shaft comprises a flat shape (see also below) comprising an outer surface. Especially, at least a part of the outer surface comprises the screw-thread. Especially the screw-thread is configured at two opposite sides of the outer surface (of such flat threaded shaft), especially having a longitudinal axis of the threaded shaft between said opposite sides. In embodiments, the threaded shaft has a cross sectional area (perpendicular to the longitudinal axis of the threaded shaft) comprising a rectangular shape, especially comprising the screw-thread at two opposite sides of the rectangular shape. In further embodiments, said cross sectional area comprises an oval shape. Yet, in further embodiments the cross sectional area comprises a circular shape.

Herein the term "cross sectional area", such as the cross sectional area of the threaded shaft, may also relate to a plurality of (different) cross sectional areas. Hence, the cross sectional area of the threaded shaft may vary along the longitudinal axis of the threaded shaft.

The body axis of the device may comprise the longitudinal axis of the threaded shaft. Especially, the body axis and the longitudinal axis of the threaded shaft coincide. Further, especially the longitudinal axis of the plunger is configured essentially parallel to the longitudinal axis of the threaded shaft.

The threaded shaft may be functionally coupled to the plunger. Especially, the threaded shaft is physically coupled to the plunger. The threaded shaft may physically be connected to the plunger at a location inside the plunger. The threaded shaft may be arranged through (only) one of the ends of the plunger. Especially, the threaded shaft is fixated in the plunger. In embodiments, the plunger may rotate relatively to the threaded shaft.

The screw cap may be configured in the container part, especially preventing the screw cap substantially from moving. Especially, the screw cap is configured preventing a movement in a direction along the longitudinal axis of the container part and especially preventing a rotational movement relative to the container wall. Hence, a rotation of the threaded shaft may be transposed (by the screw cap) in a translation of the threaded shaft (relative to the screw cap). Especially, such rotation relative to the screw cap is also relative to the plunger. In further embodiments, the screw cap may be configured not allowing a movement in a direction along the longitudinal axis of the container part and especially allowing a rotational movement relative to (/about) the longitudinal axis. Especially in such embodiment, the threaded shaft may translate and especially not rotate (when actuated).

The applicator device may further comprise an end cap. Especially, the end cap is (directly or indirectly) functionally coupled to the threaded shaft. In embodiments an actuating element is configured around the threaded shaft. Especially, the actuating element may comprise an opening, wherein the opening is configured to match the cross sectional area of the threaded shaft. The actuating element may provide the rotation of the threaded shaft (relative to the screw cap). The end cap may be functionally coupled to the actuating element. In embodiments, the end cap comprises the actuating element. In further embodiments, the end cap and the actuating element do not contact each other. The end cap is especially arranged to actuate the threaded shaft. In embodiments, a rotation of the end cap (relative to the screw cap) provides a rotation of the threaded shaft. In embodiments, a rotation of the end cap directly provides such rotation of the threaded shaft. Especially an angular displacement of the end cap provides an angular displacement of the threaded shaft to the same extent. In other embodiments, the rotation of the end cap indirectly provides the rotation of the threaded shaft. In embodiments, the angular displacement of the end cap and the angular displacement of the threaded shaft are not the same. Especially, the rotation of the end cap is proportional to the rotation of the threaded shaft (relative to the screw cap).

In other embodiments, the end cap may (directly or indirectly) be coupled to the screw cap, and especially a rotation of the end cap may provide a rotation of the screw cap. In embodiments, a rotation of the screw cap provides a translation of the threaded shaft.

In further embodiments, a translation of the end cap (relative to the screw cap) provides a rotation of the threaded shaft. Especially in such embodiments, the end cap may be functionally and/or physically coupled (especially via the actuating element) to the threaded shaft via a transposing element, transposing a translational movement is a rotational movement. Especially, such end cap may comprise a clickable end cap. Especially, the applicator device may be configured to expel a determined amount of liquid every time the end cap is clicked. In yet further embodiments, a translation of the end cap provided a rotation of the screw cap (especially providing a translation of the threaded shaft).

Hence, in embodiments, the applicator device may further comprise an end cap, functionally coupled to the threaded shaft, wherein the applicator device is configured to provide the rotation of the threaded shaft (i) based on a translation of the end cap relative to the screw cap or (ii) based on a rotational movement of the end cap relative to the screw cap.

In yet other embodiments, the plunger advance system comprises a spindle system comprising a threaded shaft, a screw cap, and a unidirectional ratchet system, and wherein the plunger advance system is configured to translate the plunger in a direction towards the valve, based on a rotation of the screw cap. Especially such embodiments may further comprise an end cap, functionally coupled to the screw cap, wherein the applicator device is configured to provide the rotation of the screw cap (i) based on a translation of the end cap relative to the screw cap or (ii) based on a rotational movement of the end cap relative to the plunger, especially relative to the container wall.

The spindle system may further comprise a ratchet system. Hence, in embodiments, the plunger advance system comprises a spindle system comprising a ratchet system. In embodiments, the ratchet system comprises a unidirectional ratchet system. Such ratchet systems are known to the skilled person, and e.g. may comprise a male element and a female element that allow rotation in one direction and prevent any rotation in the opposite direction. The ratchet system is especially a unidirectional ratchet system. The ratchet system may allow rotation of the threaded shaft in one direction. In embodiments, a rotation of the end cap in a first direction may provide a rotation of the threaded shaft, especially in the same direction (and providing a translation of the threaded shaft). In other embodiments, a rotation of the end cap in a first direction may provide a rotation of the screw cap, especially in the same direction (and providing a translation of the threaded shaft). A rotation of the end cap in the opposite direction may not provide a rotation of the threaded shaft or of the screw cap. In further embodiments, the ratchet system is configured to prevent rotation of the end cap in said opposite direction. Especially, one of the (male and female) elements is fixedly connected in the container part to a wall of the container part. In embodiments, the end cap may physically contact the other element (of the male and female elements). In further embodiments, especially comprising a clickable end cap, the other element may engage on the actuating element. Hence, the ratchet system may comprise a first element and a (complementary) second element, that especially may engage on each other.

Hence, in embodiments, the plunger advance system comprises a spindle system comprising a threaded shaft, a screw cap, and a unidirectional ratchet system, and especially wherein the plunger advance system is configured to translate the plunger in a direction towards the valve, based on a rotation of the threaded shaft.

The plunger advance system comprises a plunger advance system material. Especially, the plunger advance system material consists of a polymer material. In further embodiments, the plunger advance system material consists of a metal. Especially, a metal may also comprise a metal alloy. In yet a further embodiment, the plunger advance system material consists of ceramics.

The plunger advance system material may especially comprise polypropylene. In further embodiments, the plunger advance system material comprises ethylene chlorotrifluoro ethylene. In yet further embodiments, the plunger advance system material comprises polyoxymethylene. Especially, the plunger advance system comprises, especially consists of, polypropylene.

Especially, the spindle system comprises the plunger advance system material.

In embodiments, the spindle system comprises polypropylene. In embodiments, the threated shaft consists of polypropylene. In further embodiments, the ratchet system (also) consists of polypropylene. Yet in further embodiments, the screw cap consists of polypropylene.

Herein the term "material", such as in "plunger advance system material" may also relate to more than one (different) materials, e.g., to more than one (different) plunger advance materials. The plunger advance system may comprise, especially consist of polypropylene. In further embodiments, the spindle system comprises, especially consists of polypropylene.

In embodiments, the applicator, especially the plunger advance system comprises the second spring system. The second spring system may be configured at a position between the end cap and the ratchet system, especially providing the elements of the ratchet system to contact each other. Especially, the second spring system is a means for providing the male and the female elements of the ratchet system to contacting each other, especially to engage on each other. In specific embodiments, the plunger advance system comprises a spindle system comprising a ratchet system comprising a first element and a second element, wherein the second spring system is configured to provide the first element and the second element to engage on each other. The second spring system may further provide (directly or indirectly) a feedback to a user of the applicator when actuating the applicator (especially rotating or "clicking" the end cap), especially a tactile feedback and/or an audible feedback. Such audible feedback may be provided via the ratchet system, especially indicating an incremental rotation of the screw cap.

Hence, the plunger advance system may comprise the second spring system, especially wherein the second spring system is arranged at a side of the plunger opposite to the storage volume. Herein a side of the plunger and the opposite side of the plunger especially relate to the first end and the second end of the plunger. Especially, one of the first end and the second end of the plunger may contact the liquid, wherein the other side may not contact the liquid. Especially, the second spring system does not contact a liquid (stored in the storage volume).

In yet further specific embodiments, the second spring system is configured to provide a tactile and/or an audible feedback during a translation of the plunger relative to the valve.

In embodiments, the second spring system comprises an opening, a through-hole, in a center of the second spring system. In further embodiments, the ratchet system comprises an opening, especially a through hole in a center of the ratchet mechanism. Especially, said openings or through holes are configured parallel to the longitudinal axis of the container part. In embodiments comprising one or more of these through holes, the threaded shaft may be arranged in the through holes (that are present). The threaded shaft may hold one or more of the ratchet system and the second spring system at a determined position. Especially, the threaded shaft may define a location of one or more of the ratchet system and the second spring system.

Especially, the second spring system is configured having specific characteristics, such as dimensions (a length, a width etc.) and physical characteristics, such as a spring constant. These characteristics may be the result of the second spring material. Especially, such characteristics may be tuned by selecting a spring material comprising a metal, such as a spring steel. It however, surprisingly was found that in embodiments, applicator devices comprising a spring material consisting of (standard) spring steel were not durable (see further below).

Hence, in embodiments, the second spring system comprises a second spring material selected from the group of stainless steel types comprising molybdenum, especially at least 0.1 wt. % molybdenum, such as at least 0.5 wt. % molybdenum. Especially, the molybdenum content is equal to or less than 7 wt. %, such as equal to or lower than 5 wt. %. Such types of stainless steel are known and comprise e.g. stainless steel types 316, 316L, 317, and 317L and superaustenitic stainless steels, such as Allegheny Ludlum alloy AL-6XN and 254SMO. Stainless steel type 316 ("SS316") and type 316L ("SS316L") for instance may contain about 2-3 wt. % molybdenum. Stainless steel type 317 ("S S317") and type 317L ("SS317L") may contain 3-4 wt. % molybdenum. The molybdenum content in the second spring material is especially larger than 0 wt. %. In embodiments, the molybdenum content in the second spring material is smaller than or equal to 3 wt. %. In other embodiments, molybdenum content in the second spring material is equal to or larger than 3 wt. %.

In further embodiments, the second spring material consists of polypropylene. In yet further embodiments, the second spring material consists of a noble metal. The second spring material may consist of one or more noble metals selected from the group of ruthenium, rhodium, palladium, silver, osmium, iridium, platinum, titanium and gold. Especially, the second spring material may comprise titanium or (a) titanium alloy, even more especially a titanium alloy containing at least 0.1 wt. % ruthenium. These (noble and/or titanium) metals may offer a corrosion resistance. Such metals, though, may be difficult to source and to machine into a viable, mass production product. Such metals may especially be applied in particular embodiments. The second spring material especially consists of stainless steel, especially a molybdenum containing stainless steel, e.g., stainless steel type SS 316.

The valve is configured in the applicator device, especially to prevent a spontaneous flow of the liquid out of the applicator device. The valve may especially prevent leaking of (the) liquid. The valve may (also) prevent air entering the container (via the tip). Allowing air to contact the liquid in the container may negatively affect the quality of the liquid. The valve especially comprises a check valve. In embodiments, the valve comprises a duckbill (check) valve. In embodiments, the valve may comprise a ball check valve.

In embodiments, the valve comprises polypropylene (PP). In further embodiments, the valve comprises ethylene chlorotrifluoro ethylene (ECTFE). In embodiments the ball check valve may e.g. comprise a ball consisting of PP, or a ball consisting of ECTFE. The valve may further comprise polybutylene terephthalate (PBT). In further embodiments, the ball consists of a metal selected from the group consisting of a noble metal and stainless steel type 316. Especially, the ball check valve comprises a glass ball (a ball consisting of glass). The valve, especially the ball check valve, may further comprise the first spring system. Such spring system may be configured to push the ball in the direction of the plunger, especially wherein the valve is closed and especially (therewith) preventing air from entering the container via the valve and/or liquid from spontaneously flowing out of the container through the valve.

In embodiments, the first spring system comprises a first spring material selected from the group of stainless steel types comprising molybdenum, especially at least 0.1 wt. % molybdenum, such as at least 0.5 wt. % molybdenum. Especially, the molybdenum content in the first spring material is equal to or less than 7 wt. %, such as equal to or lower than 5 wt. %. The molybdenum content in the first spring material is especially larger than 0 wt. %. In embodiments, the molybdenum content in the first spring material is smaller than or equal to 3 wt. %. In other embodiments, the molybdenum content in the first spring material is equal to or larger than 3 wt. %. In embodiments, wherein the applicator device comprises the (first) spring system, especially (also) the first spring material consist of a molybdenum containing stainless steel (i.e. a stainless steel material comprising molybdenum), especially SS316.

In further embodiments, the first spring material consists of polypropylene. In yet further embodiments, the first spring material consists of a noble metal or a titanium alloy, like described above (in relation to the second spring material).

The spring material for the one or more spring systems may especially be selected in relation to the material of the plunger advance system.

A number of materials were tested. It surprisingly appeared that even when elements were not in contact with an acid liquid, materials appeared to show deterioration in time. For instance, metal elements not in contact with the acid, degraded with time. It further appeared that this degeneration process was essentially smaller with the herein indicated materials for the first spring material and the second spring material, such as steel, like especially steel SS316. It was e.g. surprisingly experienced that although the second spring essentially did not contact the liquid in the experiments, embodiments having (aggressive) TCA containing liquids in the storage volume and having a second spring made of normal spring steel were not very durable. Although the second spring was not contacting the liquid, the second spring was negatively affected in time. Without being bound to theory, it was hypothesized that minute amounts of TCA gasses may have been present at the side of the plunger opposite to the storage volume, especially at contacting the second spring. Due to a negative charge of TCA and a positive charge of the steel spring, ionization may occur wherein chloroform formed from TCA may attack the spring material. Although stainless steel 304 is known (e.g. from handbooks) to have an excellent compatibility with chloroform, also embodiments comprising SS 304 showed a low durability during durability tests. Springs made of SS304 could show a color change and/or corrosion in durability tests, eventually negatively affecting or even disrupting the plunger advance system, and especially not allowing to expel a controlled dose (or any dose) of the (treatment) liquid. Yet, in tests with second springs made of a molybdenum containing stainless steel, such as stainless steel grade 316, the spring material was not negatively affected when the storage volume comprised a TCA containing liquid.

Likewise, it appeared that some components when made of polymer, especially the plunger advance system, even when not being in contact with the acid liquid, show deterioration with time.

It further appeared that a combination of the spring materials as indicated herein and PP, ECTFE, or POM, especially PP, led to the best results in terms of stability, whereas when other spring materials were chosen and/or other polymers were chosen, the device had a relatively short lifetime. The required properties of the polymer material may depend on the characteristics of the liquid. Durability tests showed that especially embodiments comprising a polypropylene container and especially also a plunger advance system comprising polypropylene, could positively persist the tests, also for liquids comprising high concentrations of TCA (e.g., equal to or more than 30 wt. %, such as equal to or more than 40 wt. %, such as equal to or lower than 60 wt. %). Upon exposure to (high concentrations of) TCA, polypropylene may have changed some of the elastic/rigidness properties of polypropylene. However, this did not negatively affect the usability and safety of the applicator device. Yet, especially, during durability tests at high concentrations of TCA, elements of the applicator device made of the polyethylene, polyoxymethylene showed partly dissolution and/or disintegrating, especially negatively affecting the usability and safety of the applicator device. Further tests performed with polyether ether ketone (PEEK) or polyvinylidene fluoride (PVDF) comprising polymer material also did not show a long time durability. Yet, elements made of ethylene vinyl acetate did not seem to be negatively affected by high concentrations of TCA (see also below).

In embodiments, the applicator device may be configured for containing TCA at a concentration equal to or more than 40 wt. %. In further embodiments, the applicator device may be configured for containing TCA at a concentration equal to or less than 40 wt. %, however, especially at least 0.5 wt. %, such as at least 1 wt. %. In embodiments, the device may be configured for a containing TCA at a concentration selected in the range of 0.5-40 wt. %. In embodiments, the device comprises TCA in a concentration selected in the range of 0.5-40 wt. %. In further embodiments, the applicator is configured for containing TCA at a concentration selected in the range of 15-25 wt. %. Especially, the liquid comprises TCA at a concentration described above. The liquid may also be indicated as "treatment liquid". The liquid may also be indicated as "composition".

Especially, (the applicator is configured such that) a rotation of the threaded shaft may advance the plunger, especially in a direction towards the valve, especially for expelling at least part of the liquid. The rotation (of the treaded shaft) may especially comprise an incremental rotation. An incremental rotation of the threaded shaft may provide an incremental translation of the threaded shaft, and especially it may provide an incremental amount of liquid being expelled. Said screw-thread may comprise a metric screw-thread. Said screw-tread may also comprise other types of standard screw-threads known in the art, such as unified screw-thread, square screw-thread, buttress screw-thread, UTS, or ACME screw-thread. Especially, the screw-thread of the screw cap matches the screw-thread of the threaded shaft, allowing engagement of the two screw-threads on each other. In embodiments, the fit of the two threads (an internal thread of the screw cap and an external thread of the threaded shaft) is determined by the international standards, such as the Metric standard. In further embodiments, the screw-thread of the threaded shaft is changed compared to the standard. In embodiments, a form of a crest of the external thread and/or a root of the internal thread is/are smoothened, especially rounded off. In embodiments, a first angle of the internal thread may differ from a first angle of the external thread and/or a second angle of the internal thread may differ from a second angle of the external thread. Such (first and second) angle may be defined by (a surface of) the thread and a plane perpendicular to the longitudinal axis of the threaded shaft (or a longitudinal axis of the screw cap). Such angle may relate to a slope of the thread, especially a slope at the first side (flank) and/or a slope at the second side (flank) of the thread. For instance for a V-type thread said angles all (for both the external thread and the internal thread) may substantially equal 30°. In embodiments the difference between said first angles and/or the difference between said second angles is selected in the range of 1°-15°, such as 1°-10°, especially 1°-5°. In embodiments, the thread is substantially symmetrical. Especially, the slope at the first side of the thread substantially equals the slope at the second side of the thread. The first side (flank) of the thread may be configured mirror-symmetrically (about an axis of symmetry) to the second side (flank) of the thread. In further embodiments, the first side and the second side of the thread are not configured mirror-symmetric. Especially the external thread is not configured mirror-symmetric. Especially the slope at the first side (flank) of the external thread is not equal to the slope at the second side (flank) of the thread. In embodiments (of the threaded shaft) the second angle that is selected is larger than the first angle. In embodiments, the first angle is selected in the range 10-45°, such as 10-40°, especially 10-20°, wherein the second angle is 1-30°, such as 1-20, especially 3-15° larger than the first angel. It was surprisingly found that in such (non-symmetric) embodiments, a polypropylene threaded shaft and a polypropylene screw cap may be rotated (relatively to each other) more easily compared to embodiments comprising a mirror-symmetric thread. Especially, such embodiment, may be more durable, and especially may suffer less from wear.

Especially such embodiment may provide a reduced resistance to rotating the threaded shaft in the screw cap. Especially, such embodiment may comprise a polypropylene screw cap and a polypropylene threaded shaft. Additionally, the threaded shaft may comprise a flat surface (see also above). The threaded shaft may, e.g., comprise a rectangular cross section wherein the thread is located at a part of the periphery of the cross section, especially at two opposite sides of the periphery. Especially, such configuration may, further reduces the resistance to rotating (and wear). Embodiments comprising a polypropylene screw cap and a polypropylene threaded shaft comprising a standard type of (internal and external) screw-thread, such as metric screw-threads or buttress screw-threads may require more heavy-duty elements in the plunger advance system to provide a durable and effective applicator. Especially, a standard type of screw-thread may comprise a mirror-symmetric screw-thread. Hence, in embodiments, the internal thread comprises a standard type (standardized) screw-thread, wherein the external thread comprises a modified (standardized) screw-thread, especially wherein said screw-thread is not mirror-symmetric. In other embodiments, the external thread comprises a standard type (standardized) screw-thread, and the internal thread comprises said modified screw-thread. Yet in further embodiments both screw-threads are modified, especially slightly in a different way to provide the reduced resistance to rotation. Herein, a mirror-symmetric screw-thread relates to a screw-thread comprising a first flank and a second flank, wherein a first angle between the first flank and a plane perpendicular to a longitudinal axis of the screw-thread (such as a longitudinal axis of a bold or a nut) substantially equals a second angle between the second flank and said plane.

In embodiments, said angles of the internal thread (of the screw cap) are selected in the range of 45-30°, especially in the range of 30-40°, even more especially in the range of 33-37°. In further embodiments, the angles of the external thread (of the threaded shaft are (also) selected in the range of 45-30°, especially in the range of 30-40°, even more especially in the range of 33-37°. Yet, in further embodiments, a first angle (between a first flank of the (external) thread (of the threaded shaft) and a plane perpendicular to the longitudinal axis of the threaded shaft) is selected in the range of 20°-24°, especially in the range 21°-23° and a second angle between a second flank of the (external) thread and said plane is selected in the range of 13°-17°, especially in the range of 14°-16°. Especially the sum of said first angle and said second angle (of the thread of the threaded shaft) is configured to be about 37°±2°.

The screw-thread of the threaded shaft comprises a pitch length that may be substantially constant over the length of the threaded shaft. The pitch length may also vary over the length of the threaded shaft. In embodiments, the pitch length (gradually) increases from a side of the shaft configured closest to the plunger, to a side of the shaft most remote of the plunger.

The applicator may further comprise a tip base. The tip base is especially configured to comprise the applicator tip.

The tip base may be arranged to provide the fluid connection between the container part and the applicator tip. Especially, the tip base comprises a central cavity for allowing the liquid to flow from the container part to the tip. Especially, the tip base is sealingly connected to the container part. In embodiments, the tip base comprises the applicator tip. Especially, in such embodiment the liquid may be provided (to e.g. a skin) via an opening in the tip base. The applicator device may further comprise a liquid providing element comprising the applicator tip. Especially the applicator base is configured to hold the liquid providing device (comprising the applicator tip). Yet in embodiments, the applicator base may function as the liquid providing device.

A configuration of the liquid providing element (or the absence of such element as such) may be selected based on, e.g., an application, a dosage (regime) and/or a use of the applicator pen. Especially the opening in the tip base comprises the application tip. The liquid providing element may comprise a brush (liquid providing element). In further embodiments, the liquid providing element comprises a nib. In further embodiments, the liquid providing element comprises a tip tube comprising (a fluid channel and) a tip tube opening.

The liquid providing element (e.g. the tip tube) may comprise a circular shape. The tip device may also comprise an oval shape. In yet further embodiments, the liquid providing element comprises a rectangular shape. Essentially, the liquid providing element may comprise any arbitrary shape. Especially, a shape of the applicator tip corresponds to the shape of the liquid providing element (or the tip base). The liquid providing element, especially at the applicator tip, may comprise a characteristic dimension, such as a diameter or a width. Especially such characteristic dimension may be selected in the range of 0.5 mm-10 mm, such as 0.5 mm-5 mm, especially 1-5 mm. The applicator is especially configured to allow replacing the liquid providing element. In embodiments, the applicator comprises a holding reference ring providing an aligned arrangement of the tip device, especially the liquid providing element. The holding reference ring may function as a reference for automatic filling line properties. In such filling line the liquid providing element may be automatically centered and may be arranged to the container part by a simple pressure tool. Especially, the liquid providing element comprises a brush. In embodiments, the brush comprises fibers. Especially, the fibers are held together by a resin. In embodiments, the brush (liquid providing device) comprises polybutylene terephthalate. In other embodiments, the liquid providing element comprises polypropylene.

Especially, the applicator tip, especially the liquid providing element, comprises a precise dosage controlled liquid providing element (at the applicator tip). In embodiments, the precise dosage controlled liquid providing element is a tube. The tip tube especially comprises a single opening (for expelling the liquid)

The applicator may further comprise a closure cap. Especially the closure cap may enclose the liquid providing element and/or the tip base. The closure cap may further enclose a part of the container. Such closure cap may be configured to prevent the applicator from leaking. Additionally, the closure cap may be configured to prevent the applicator form any loss of treatment liquid due to vaporization. Such closure cap may be configured to prevent the applicator from drying. Such closure cap may prevent the tip device, especially the nib or the brush, from drying. Such closure cap may further prevent the liquid in liquid providing element and/or in the remainder of the applicator from being oxidized. For instance, air surrounding the applicator may (otherwise) oxidize the liquid in the liquid providing element and/or in the tip base and other parts of the applicator. In embodiments, the closure cap comprises a closing system inside the closure cap, especially configured to closely fit the tip base and/or the liquid providing elements. In embodiments, the closure cap comprises a child safe closure cap. Especially, the closure cap and the tip base and/or the container may comprise safety elements preventing a child to remove the closure cap from the remainder of the applicator. In further embodiments, the closure cap and the container comprise visual elements, especially arrows, which have to be aligned to remove the closure cap.

In a specific embodiment the applicator device comprises an applicator tip and a container part, wherein the container part comprises: (i) a container comprising a container wall, a valve, and a plunger, wherein the container wall, the valve, and the plunger together define a storage volume for containing a liquid, wherein the plunger comprises a circumferential wall, sealingly contacting the container wall; and (ii) a plunger advance system functionally coupled to the plunger and configured to advance the plunger for reducing the storage volume for expelling at least part of the liquid via said valve to said tip, wherein the plunger advance system is arranged outside the storage volume; wherein (iii) (a) the valve comprises a first spring system comprising a first spring material comprising a stainless steel material comprising a molybdenum content selected in the range of 0.5-7 wt. %, and (b) the plunger advance system comprises a second spring system comprising a second spring material comprising a stainless steel material comprising a molybdenum content selected in the range of 0.5-7 wt. %, applies; and (iv) the plunger advance system comprises a polymer selected from the group consisting of polypropylene, ethylene chlorotrifluoroethylene, and polyoxymethylene (especially polypropylene); and wherein the plunger advance system comprises a spindle system comprising a ratchet system comprising a first element and a second element, wherein the second spring system is configured (arranged) to provide the first element and the second element to engage on each other.

The invention further provides such treatment liquid especially for use in the treatment of a wart (or corn). In a specific embodiment, the composition may further comprise vitamin A. In yet a further embodiment, the treatment liquid further comprises vitamin A. The acid in the treatment liquid is especially applied to peel the skin or mucous membrane, especially the skin, by which the skin or mucous membrane may renew itself.

The applicator or the treatment liquid may be used for several types of lesions. The applicator, or the treatment liquid, may be applied for medical use and/or non-medical use, such as cosmetic use. Herein, the term "treatment liquid" refers to the "liquid". The liquid may comprise the acid, especially TCA and optionally one or more other components.

In a further aspect, the invention especially provides the use of the applicator, as defined herein, for a (cosmetic) treatment. In embodiments, the use is related to a (cosmetic) treatment of a topical lesion selected from the group consisting of epidermodysplasia veruciformis, a HPV (human papillomavirus) caused skin disorder, acne, a scar, a wrinkle, a tattoo, eyelid xanthelasma, an age spot, a senial lentigo, a solar lentigo, a melasma, a hand wart, a plantar wart, a corn, an ingrown toe nail, a nail dystrophy, a nail fungus, a mucous membrane lesion, stomatitis. The term "wart" may e.g. relate to one or more of verruca vulgaris and verruca plantaris. The treatment liquid is especially suitable for the treatment of one or more of a wart and a corn. Likewise, also the treatment liquid per se may be used. Especially, the use is related to one or more treatments selected from the group consisting of a skin treatment, a nail treatment, a mouth treatment, an ear care (treatment), an eye care (treatment). The term "mouth treatment" may relate to mouth ulcers, teething babies, teeth whitening, and ingrown nails. Ear care may, e.g., relate to an ear infection, blocked ears, and ear cleaning. Eye care may, e.g. relate to dry eyes, irritated eyes, and red eyes.

Hence, the invention provides in yet a further aspect also the use of the treatment liquid as defined herein, for a cosmetic treatment (or a medical treatment) of a topical lesion selected from the group consisting of epidermodysplasia veruciformis, a HPV caused skin disorder, acne, a scar, a wrinkle, a tattoo, eyelid xanthelasma, an age spot, a senial lentigo, a solar lentigo, a melasma, a hand wart, a plantar wart, a corn, an ingrown toe nail, a mucous membrane lesion.

The term topical treatment especially relates to the treatment with the treatment liquid to a (body) surface, such as the skin, the nail or a mucous membrane, especially the (human) skin. In embodiments, the treatment especially relates to a nail treatment or a mouth treatment.

The treatment liquid, especially the acid may comprises one or more acids selected from the group consisting of trichloro acetic acid, salicylic acid, formic acid, glycolic acid, dichloro acetic acid, monochloro acetic acid, boric acid, nitric acid, sulfuric acid, phosphoric acid, oxalic acid, lactic acid, hydrochloric acid. Even more especially, the treatment liquid comprises at least trichloro acetic acid (TCA). Hence, the acid may also comprise a combination of two or more different acids.

Of course, the treatment liquid may optionally comprise one or more other ingredients, including one or more other active ingredients. The composition as described herein may comprise other ingredients commonly used in cosmetics and pharmaceutical products, such as one or more of a surfactant, a colorant and a perfume.

Trichloroacetic acid (TCA) in the treatment liquid as described herein, proved to be effective against a plethora of skin lesions, in particular warts, corns and calluses, molluscum contagiosum, acne, skin hyperpigmentation, actinic keratosis as well as nail lesions including ingrown toenails and onchyomycosis, and lesions in mucous membranes such as mouth ulcers and cold sores. Application of trichloroacetic acid is particularly effective against genital warts, and especially against ano-genital warts where it has been studied in comparative trials where its effectiveness was compared with other anti-wart therapies. In addition, TCA application was effective on various other skin disorders, in particular: epidermodysplasia veruciformis—skin disorder also caused by HPV virus, acne, to remove acne scars and wrinkles, tattoo removal, eyelid xanthelasma, age spots, senial lentigo and solar lentigo, melasma.

In a specific embodiment, the acid comprises one or more acids selected from the group consisting of trichloro acetic acid, salicylic acid, glycolic acid, dichloro acetic acid, monochloro acetic acid, boric acid, nitric acid, sulfuric acid, phosphoric acid, oxalic acid, and lactic acid.

Additionally or alternatively, the treatment liquid may comprise one or more of formic acid and salicylic acid, which alone or in combination may also provide a good result. Hence, in an embodiment, the treatment liquid comprises TCA, and optionally formic acid, and in another embodiment, the treatment liquid comprises formic acid, and optionally TCA.

Salicylic acid has a positive effect in treating skin and nails. In addition to that, salicylic acid gives a mild anaesthetic effect. Salicylic acid in combination with TCA showed a synergistic effect against skin lesions and nail lesions. Another advantage is that using a combination of salicylic acid and TCA allows for a composition with a relatively low concentration of each of salicylic acid and TCA with a similar effect to compositions using only TCA or only salicylic acid. Using the relatively low concentrations of TCA and salicylic acid decreases the chance of skin irritation due to either of these compounds. Moreover, salicylic acid diminished the discomforting burning feeling on skin and nails sometimes experienced by persons treated with products containing substantial amounts of TCA.

The treatment liquid may thus amongst others be used in for instance a skin peeling treatment, for the medical or cosmetic treatment of a skin lesion selected from the group consisting of warts, corns and calluses, and for nail treatments including ingrown toenails. A postulated mechanism of action is that the composition comprising TCA, or another acid, softens the skin or nail, and enables to peel the skin or nail lesion away. For severe lesions, multiple treatments may be needed. Both cosmetic and medical treatments may be performed with the compositions according to the invention. Other active ingredients contributing to the treatment of the lesion may be added. For instance salicylic acid (see also above) is another component effective in corroding the skin or nails, and may be used as an additional active ingredient in combination with trichloroacetic acid.

Hence, the invention further provides the use of a treatment liquid for the cosmetic treatment of the human skin. Especially, the composition is used for a skin peeling treatment or the treatment of a skin lesion selected from the group consisting of warts, corns and calluses. The compositions are particularly effective against warts and related lesions, including viral warts, verrucae, and water warts (molluscum contagiosum). These treatments are typically considered cosmetic treatments rather than medical treatments. The invention also provides the use of a composition as described herein for the cosmetic treatment of nails. In particular nail deformations (for instance as a result from onchyomycosis) and ingrown toenails may be treated effectively.

The invention further provides the use of a treatment liquid or treatment composition as described herein for the treatment of lesions in mucous membranes, in particular mouth ulcers and cold sores. The invention further provides the use of the treatment liquid or treatment composition as described herein for the cosmetic treatment of superficial lesions selected from the group consisting of viral warts, verrucae, water warts (molluscum contagiosum), corns and calluses, and age spots, solar lentigo, senial lentigo, acne, mouth ulcers (canker sores), cold sores and ingrown toenails The treatment liquid especially comprises an aqueous liquid, such as especially water, and the acid. Especially, the total amount of other components in the treatment liquid, other than the acid and the liquid, such as the aqueous liquid, is less than 10 wt. %, especially less than 5 wt. %, examples of other compounds, such as a colorant or a perfume, are mentioned above. Especially, the treatment liquid comprises the acid in a concentration up to 40 wt. %, such as at maximum 35 wt. %, even more especially at maximum 20 wt. %. Higher acid concentrations may lead to undesired topological effects and/or may be unsafe, such as in the kind of application with children or specific topical parts, like mucous membrane. In a specific embodiment, the treatment liquid comprises the acid in a concentration in the range of 1-10 wt. %. Lower concentrations than 1 wt. % may not be effective enough. Especially, the concentration of the acid in the treatment liquid is at least 2 wt. %, even more especially at least 3 wt. %.

The applicator may especially be configured to provide a single dose of in embodiments not more than 1 ml, such as especially not more than 0.75 ml, such as 0.1-0.5 ml, like 0.1-0.2 ml, or less than 0.2 ml. As will be known by the person skilled in the art, this can be tuned by amongst others the dimensions of the liquid providing element, such as brush dimensions, the angular displacement, the pitch of the threaded shaft. A dosage valve or dosage application may be used to control that the desired dose is substantially always met.

As indicated above, especially polypropylene may be used for one or more elements of the applicator device. The applicator device may comprise, especially substantially consist of, polymer material and metal material (such as for the spring system), (and additionally some minor elements comprising other material, such as a glass ball in the valve). In embodiments, the polymer material comprises polypropylene and ethylene vinyl acetate, especially wherein the metal material comprises a molybdenum containing stainless steel, especially SS316. In further embodiments, (only) the plunger comprises ethylene vinyl acetate. In embodiments the first spring material and especially also the second spring material is a molybdenum containing steel, such as SS 316. In a specific embodiments, the applicator device comprises a polymer material and a metal material, wherein the polymer material consists of polypropylene and ethylene vinyl acetate, wherein the plunger comprises (consists of) the ethylene vinyl acetate and wherein the metal material consists of a molybdenum containing steel, especially SS316.

In a specific embodiment, the container wall and the spindle system comprise, especially consist of, polypropylene, especially wherein the plunger comprises, especially consists of, ethylene vinyl acetate, and especially wherein the first spring material and the second spring material comprise, especially consist of, a molybdenum containing steel, especially SS 316.

The polypropylene polymer may e.g. be selected from the type of homopolymer, random copolymer, and block copolymer. The copolymer is typically used with ethylene. Likewise, the polyethylene polymer may e.g. be selected from the type of homopolymer, random copolymer, and block copolymer.

In an embodiment, the treatment liquid may further comprises vitamin A. Vitamin A is a retinoid, which may act to affect HPV induced lesions to prevent recurrence of the virus. Vitamin A may evoke or potentiate immune response to warts and thus is combination with the described composition, treatment may be more effective when vitamin A is included. Hence, vitamin A may promote healing and/or prevent reoccurrence of the skin lesion, especially warts.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to an advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily to scale.

DETAILED DESCRIPTION OF THE EMBODIMENTS

Figure 1:
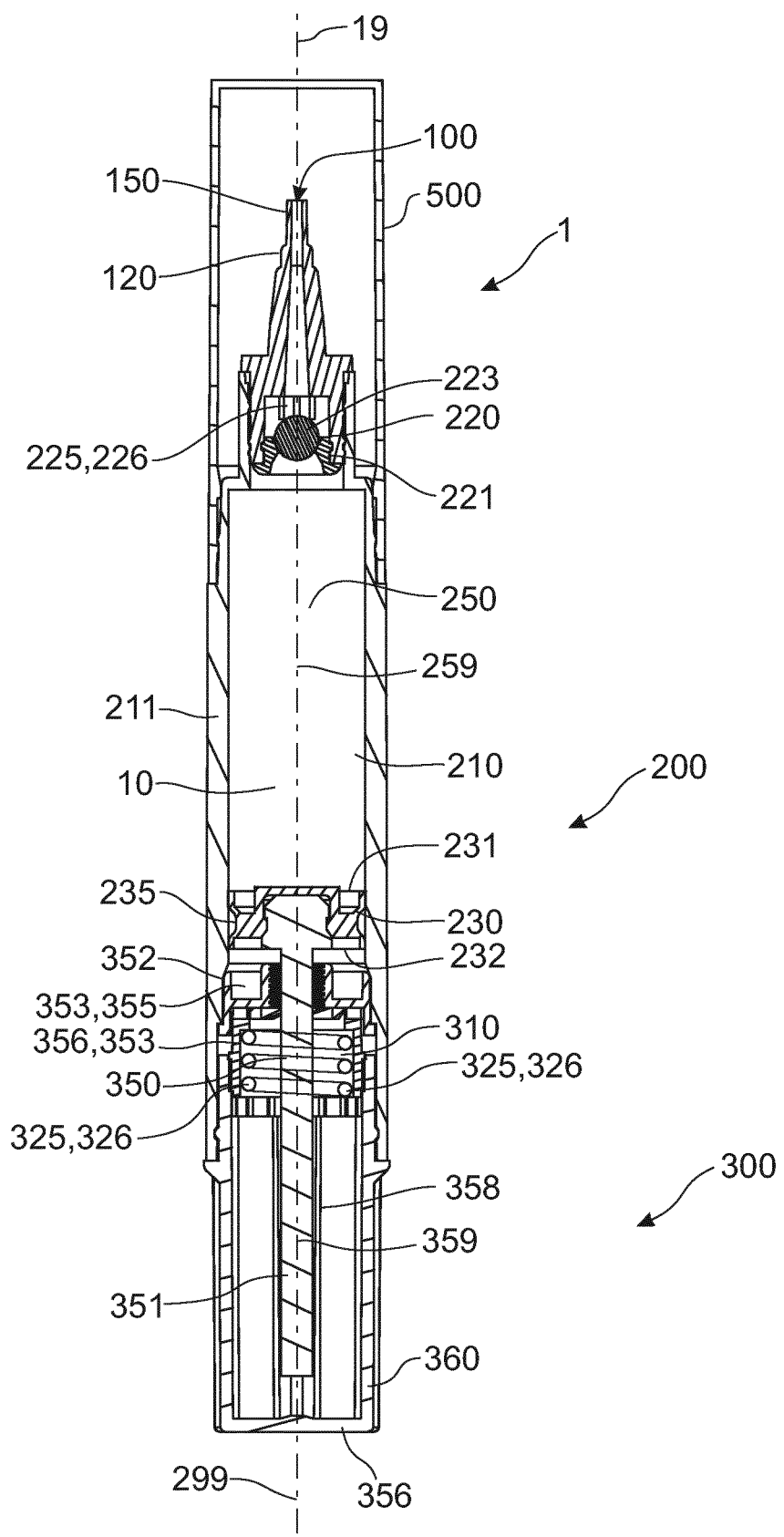
FIGS. 1 and 2 schematically depict embodiments of the applicator.

FIG. 1 schematically depicts an embodiment of the applicator device 1. The embodiment depicted in FIG. 1 is an embodiment wherein the applicator 1 may be actuated by a rotation of the end cap 360. The embodiment depicted in FIG. 2 may be actuated by a translation of the end cap 360. The applicator 1 comprises an applicator tip 100 and a container part 200. Especially, the applicator tip 100 depicts an extreme of the applicator 1 when the closure cap 500 is removed. The figures further depict the device body axis 19.

The container part 200 comprises a container 210 especially for containing a (treatment) liquid 10 in a storage volume 250. Herein the term "composition" may also be used for the liquid 10. The container part 200 comprises a longitudinal axis 299, or body axis 299. The storage volume 250 is a variable storage volume 250 and is defined by the container wall 211, the valve 220, and the plunger 230. Note: in FIG. 2, only the location of the valve 220 is depicted; the valve 220 is not directly pictured. The plunger 230 may be translated (along the longitudinal axis 259 of the storage volume 250) in the direction of the valve 220 by means of the plunger advance system 300, functionally coupled to the plunger 230, wherein the storage volume 250 reduces and at least a part of the liquid 10 (if contained in the container 210) may be expelled from the storage volume 250 via the valve 220.

Figure 2:
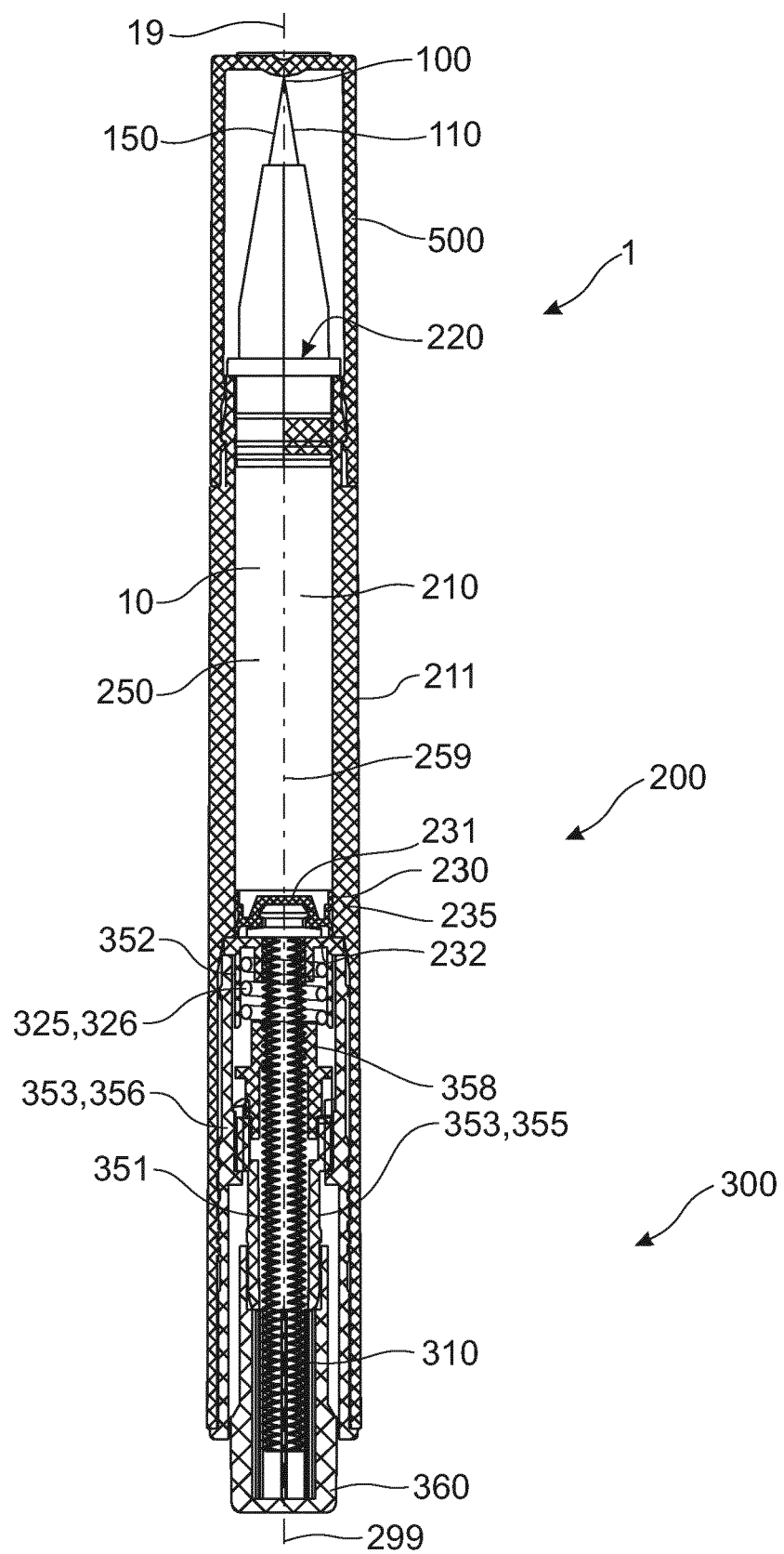

In both embodiments of FIG. 1 and FIG. 2, the plunger advance system 300 is arranged outside the storage volume 250 and hence especially does not contact the liquid 10. The applicator 1 is configured such that when moving the plunger 230 (also) no liquid 10 may pass the circumferential plunger wall 235. This circumferential wall 235 sealingly contacts the container wall 211. The plunger 230 may comprise polypropylene (PP) or ethylene vinyl acetate (EVA). Especially, the plunger 230 comprises ethylene vinyl acetate (EVA). FIG. 1 further depicts the plunger 230 comprising a double-cone shape, especially wherein the plunger wall 235 comprises a concave shape. Also in the embodiment, the plunger 230 comprises a concave first end 231 and a concave second end 232 (see also FIG. 3a-b). The plunger advance system 300 especially comprises a spindle system 350 comprising a ratchet system 353 comprising a first element 355 and a second element 356 that may be forced to each other (and allowing them to engage) by the second spring system 325.

The depicted embodiments comprise a ratchet system 353 comprising two elements 355, 356 (configured as a female and a male element). Both embodiments comprise the second spring system 325, especially configured to force the elements 355, 356 of the ratchet system 353 towards each other, allowing one element 356 to engage on the other element 355. By engaging the male and the female elements 355, 356, a rotation (of the threaded shaft 351) in one direction may be prevented and especially a rotation in the opposite direction may be allowed. In embodiments, the second spring system 326 comprises a second spring material 326 such as a noble metal, or a stainless steel material comprising a molybdenum content selected in the range of 0.5-7 wt. %. In specific embodiments, second spring material 326 comprises a molybdenum comprising stainless steel, such as stainless steel type 316 (SS316) or the like. In the embodiments depicted, the second spring system 325 is arranged at the side of the plunger 230 opposite to the storage volume 250. Hence, especially the liquid 10 may not contact the second spring system 325. The second spring system 325 may be configured to provide (directly and/or indirectly) a tactile and and/or audible feedback when the applicator 1, especially the plunger 230 is actuated. The audible feedback may directly be provided by the elements 355, 356 of the ratchet system 353. When the applicator is actuated, the plunger 230 may translate relative to the valve 220.

FIG. 1 further depicts an embodiment comprising the first spring system 225 comprising the first spring material 226. In embodiments (also) the first spring material 226 comprises, especially consists of, SS316. In this embodiment, the valve 220 comprises a ball check valve 221 comprising the first spring system 225. The ball check valve 221 further comprises a ball, such as a glass ball 223. The valve 220 especially has a closed position (depicted in FIG. 1) wherein the applicator tip 100 is in closed fluid connection with the storage volume 250 and an open position wherein the applicator tip 100 is in (open) fluid connection with the storage volume 250. By translating the plunger 230, the force on the ball valve provided by the treatment liquid 10 may be larger than the (counter acting) spring force of the spring system 225 and the valve 220 may comprise the open position.

The plunger advance system 300 in FIGS. 1 and 2 comprises a spindle system 350 comprising a threaded shaft 351 (comprising a longitudinal axis 359), a screw cap 352, and a unidirectional ratchet system 353 (and comprising the female (or first) and male (or second) elements 355, 356), and optionally an actuating element 358 (see further below). The plunger advance system 300 may comprise a polymer 310, such as a polymer 310 selected from the group consisting of polypropylene (PP) and polyoxymethylene (POM) and ethylene vinyl acetate (EVA). Especially one or more of the above described elements 351, 352, 353 and 358 of the plunger advance system 300 comprises the polymer 310. In embodiments, at least one of these elements 351, 352, 353, 358 especially all elements 351, 352, 353 and optionally 358 consist of polypropylene. In further embodiments, at least one of these elements 351, 352, 353, 358 consist of ethylene vinyl acetate. In further embodiments the container 210, especially the container wall 211 (also) comprises, especially consist of, polypropylene. Especially all elements 351, 352, 353 and optionally 358 consist of ethylene vinyl acetate.

The plunger advance system 300 is especially configured to translate the plunger 230 in a direction towards the valve 220, based on a rotation of the threaded shaft 351, especially to transport the liquid 10 in a direction of the tip 100.

The applicator devices 1 depicted in FIGS. 1 and 2 further comprise an end cap 360 that is functionally coupled to the threaded shaft 351. The embodiment depicted in FIG. 1 is configured to provide the rotation of the threaded shaft 351 based on a rotational movement of the end cap 360 (relative to the screw cap 352). The embodiment depicted in FIG. 2 is a clickable embodiment, wherein the rotation of the threaded shaft 351 is based on a translation of the end cap 360 (relative to the screw cap 352). The screw cap 352 may be fixed to a wall of the container part and may not move (translate or rotate) with respect to said wall. Hence, a rotation of the threaded shaft 351 may be transposed by the screw cap 352 into a translation of the threaded shaft 351 with respect to the screw cap 352.

The actuation of the end cap 360 may be transposed to the threaded shaft 351 via an actuating element 358 that is arranged around the threaded shaft 351. Such actuating element 358 may provide a rotation to the threaded shaft 351 by rotating (itself). In the embodiment of FIG. 1, the end cap 360 comprises the actuating element 358. In the clickable embodiment of FIG. 2, the element 356 of the ratchet system 353 may engage on the actuating element 358 when the end cap 360 is actuated.

The applicator 1 may further comprise a liquid providing element 150. Such liquid providing element 150 may provide the liquid 10 to an area to be treated, e.g. a skin or a nail. The liquid providing element may e.g. comprise a tip tube 120, a brush 110, or a nib. The liquid providing element 150 may comprise the applicator tip 100.

The applicators depicted in FIGS. 1 and 2 comprise an elongated shape, especially comprising a pen shape. In such embodiments, the device body axis 19, the longitudinal axis 259 of the storage volume 250, the longitudinal axis 359 of the threaded shaft 351 and the longitudinal axis 299 of the container part 200, also referred herein as container part body axis 299 may coincide.

Figure 3A:
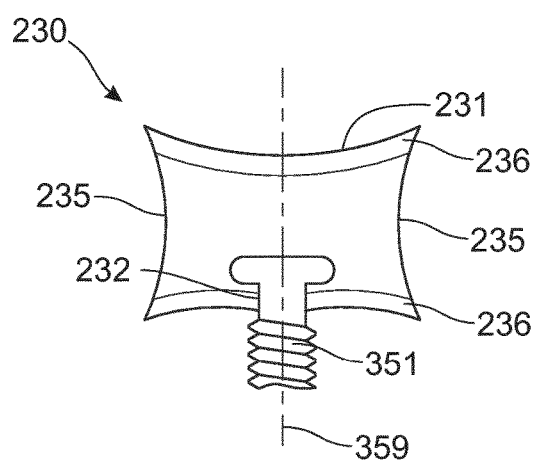
FIGS. 3a and 3b schematically depict embodiments of the plunger.
Figure 3B:
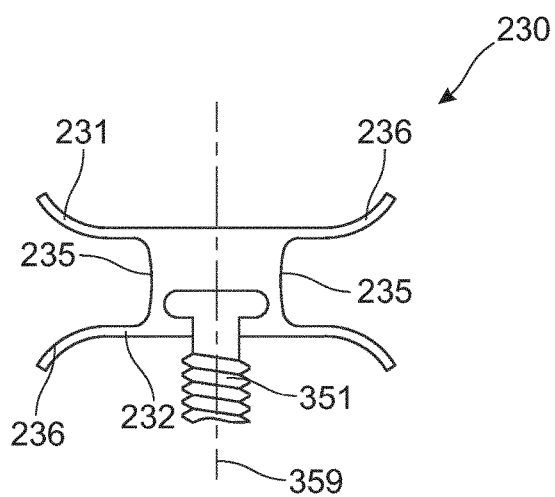

In FIGS. 3a and 3b embodiments of the plunger 230 are depicted. The figures depict different embodiments of the plunger 230 comprising a double-cone shape, especially wherein the circumferential plunger wall 235 comprises a concave shape. The plunger 230 comprises a concave first end 231 and a concave second end 232. In the embodiments, the first and the second end 231, 232 are reinforced by configuring the circumferential wall 235 thicker at a location 236 at the ends 231, 232

Figure 4:
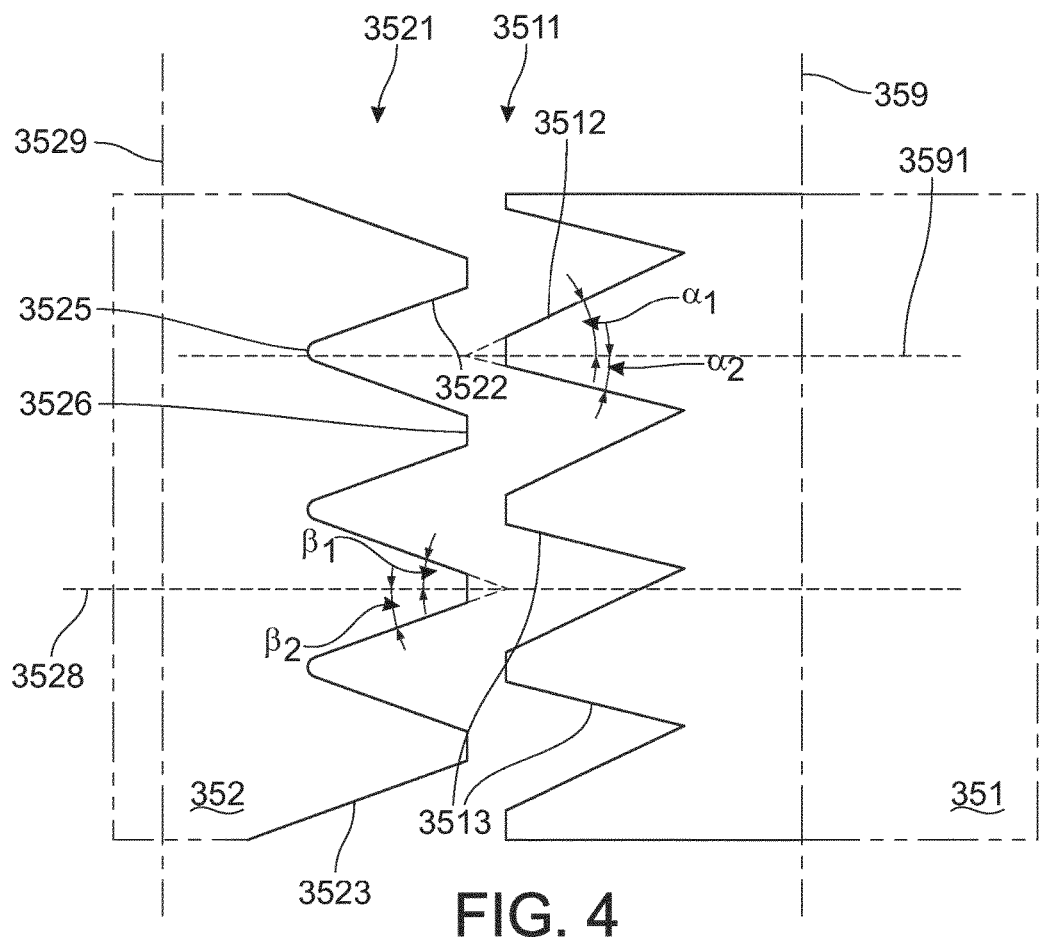
FIG. 4 schematically depicts some further aspects of the spindle system.

FIG. 4 schematically depicts an aspect of the spindle system comprising a modified screw-thread. In the figure a part of a screw cap 352, comprising the internal thread 3521 and a threaded shaft 351 comprising the external thread 3511 are depicted. In a standardized thread a first angle α1 between a first flank 3512 of the external thread 3511 and a plane 3591 perpendicular to the longitudinal axis 359 of the threaded shaft 351 may be equal to a second angle α2 between the second flank 3513 of the external thread 3511 and the plane 3591. Likewise, a first mating angle β1 between a first mating flank 3522 of the internal thread 3521 and a mating plane 3528 perpendicular to a longitudinal axis 3529 of the screw cap 3512 and a second mating angle β2 between a second mating flank 3523 of the internal thread 3521 and the mating plane 3528. Especially, the first angle α1 and the first mating angle β1 may be substantially equal. Especially (also) the second angle α2 and the second mating angle β2 may be substantially equal.

In a modified thread, the first angle α1 and/or the second angle α2 may be changed (adapted), wherein the first angle α1 is larger than the second angle α2 or wherein the second angle α2 is larger than the first angle α1. Alternatively or additionally, the first mating angle β1 and/or the second mating angle β2 may be changed, wherein the first mating angle β1 is larger than the second mating angle β2 or wherein the second mating angle β2 is larger than the first mating angle β1.

In embodiments the (first and second) mating angles β1 and β2 are substantially equal. In embodiments the mating angles β1 and β2 are selected in the range of 45-30°, especially in the range of 30-40°, even more especially in the range of 33-37°. In further embodiments, the (first and second) angles are selected in the range of 45-30°, especially in the range of 30-40°, even more especially in the range of 33-37°. Yet, in further embodiments, the first angle α1 (between the first flank 3512 of the external thread 3511 and the plane 3591) is selected in the range of 20°-24°, especially in the range 21°-23° and the second angle α2 (between the second flank 3513 of the external thread 3511 and the plane 3591) is selected in the range of 13°-17°, especially in the range of 14°-16°. Especially the sum of the first angles α1 and the second angle α2 is about 37°±2°. Especially, the sum of the first mating angle β1 and the second mating angle β2 is about 70°±2°.

In the figure, further some flattened/rounded crests 3526 and roots 3525 are also depicted. The applicator device 1 according to the invention may especially be configured for containing trichloro acetic acid (TCA) at a concentration equal to or less than 40 wt. %. The applicator may be used for a (cosmetic) treatment, e.g. in a skin treatment, a nail treatment, a mouth treatment, or for ear care (treatments), and eye care (treatments).

Furthermore, due to strong exfoliating properties of the treatment liquid in combination with the applicator the applicator may also advantageously be applied for precise corrections for tattoo removal, skin tags or other skin related corrections.

The invention claimed is:

1. An applicator device comprising an applicator tip and a container part, wherein the container part comprises:
   (i) a container comprising a container wall, a valve, and a plunger, wherein the container wall, the valve, and the plunger together define a storage volume for containing a liquid, wherein the plunger comprises a first end, a second end and a concavely shaped circumferential wall bridging the first and second ends, wherein the circumferential wall sealingly contacts the container wall, and wherein during use the first end contacts the liquid and the second end does not contact the liquid; and
   (ii) a plunger advance system functionally coupled to the plunger and configured to advance the plunger for reducing the storage volume for expelling at least part of the liquid via said valve to said tip, wherein the plunger advance system is arranged outside the storage volume; wherein
       (a) the valve comprises a first spring system comprising a first spring material comprising a stainless steel material comprising a molybdenum content in a range of 0.5-7 wt. %, and wherein
       (b) the plunger advance system comprises a second spring system comprising a second spring material comprising a stainless steel material comprising a molybdenum content in a range of 0.5-7 wt. %, and wherein
       (c) the plunger advance system comprises a polymer selected from the group consisting of polypropylene (PP), ethylene chlorotrifluoroethylene (ECTFE), and polyoxymethylene (POM); and wherein
       (d) the plunger advance system comprises a spindle system comprising a ratchet system comprising a first element and a second element, wherein the second spring system is configured to provide the first element and the second element to engage on each other.

2. The applicator device according to claim 1, wherein in an open position of the valve the applicator tip is in fluid connection with the storage volume, and wherein in a closed position of the valve said fluid connection is intercepted.

3. The applicator device according to claim 1, wherein the plunger comprises ethylene vinyl acetate (EVA), and wherein the plunger advance system comprises polypropylene, and wherein the container wall comprises polypropylene.

4. The applicator device according to claim 1, wherein the spindle system further comprises a threaded shaft, a screw cap, and a unidirectional ratchet system, and wherein the plunger advance system is configured to translate the plunger in a direction towards the valve based on a rotation of the threaded shaft.

5. The applicator device according to claim 4, further comprising an end cap, functionally coupled to the threaded shaft, wherein the applicator device is configured to provide the rotation of the threaded shaft based on (i) a translation of the end cap relative to the screw cap or based on (ii) a rotational movement of the end cap relative to the screw cap.

6. The applicator device according to claim 1, wherein the second spring material consist of stainless steel type 316.

7. The applicator device according to claim 1, wherein the second spring system is configured to provide a tactile and/or an audible feedback during a translation of the plunger.

8. The applicator device according to claim 1, wherein the first spring material consists of stainless steel type 316.

9. The applicator device according to claim 1, wherein the valve comprises a ball check valve.

10. The applicator device according to claim 9, wherein the ball check valve comprises a glass ball.

11. The applicator device according to claim 1, wherein each of the first end and the second end is concave.

12. The applicator device according to claim 1, containing trichloro acetic acid (TCA) at a concentration in a range of 0.5-40 wt. %.

13. The applicator device according to claim 1, wherein the liquid comprises a gel having a viscosity measured at 25° C. of 2500-10000 mPa·s.

14. The applicator device according to claim 13, wherein the liquid comprises trichloroacetic acid and carbopol.

15. The applicator device according to claim 14, wherein the liquid comprises the trichloro acetic acid (TCA) at a concentration in a range of 0.5-40 wt. %.

16. The applicator device according to claim 4, wherein the threaded shaft comprises an external thread, wherein
  a first angle of the external thread between a first flank of the external thread and a plane perpendicular to a longitudinal axis of the threaded shaft is in a range of 10-45°, and wherein
  a second angle of the external thread between a second flank of the external thread and the plane perpendicular to the longitudinal axis of the threaded shaft is 1-30° larger than the first angle.

17. The applicator device according to claim 16, wherein the threaded shaft comprises a polypropylene threaded shaft and wherein the screw cap comprises a polypropylene screw cap.

18. The applicator device according to claim 16, wherein the threaded shaft has a rectangular cross sectional shape perpendicular to the longitudinal axis of the threaded shaft, wherein the external thread is configured at two opposite sides of the rectangular shape of the threaded shaft.

19. The applicator device according to claim 4, wherein the threaded shaft comprises an external thread and the screw cap comprises an internal thread, and wherein a crest of the external thread and/or a root of the internal thread is smoothened.

20. A cosmetic treatment method which comprises providing the applicator device according to claim 15, and applying the liquid from the applicator device to a cosmetic treatment site.

* * * * *